United States Patent [19]

Kubota

[11] 4,346,702
[45] Aug. 31, 1982

[54] SLIP JOINT OF ENDOTRACHEAL TUBE

[76] Inventor: Yukio Kubota, No.1-12, Uenohigashi 1-chome, Toyonaka-shi, Osaka-fu, Japan

[21] Appl. No.: 212,129

[22] Filed: Dec. 2, 1980

[30] Foreign Application Priority Data

May 1, 1980 [JP] Japan ................................. 55-59004

[51] Int. Cl.³ .......................................... A61M 25/02
[52] U.S. Cl. ............................. 128/207.14; 128/912; 285/308; 285/420
[58] Field of Search ...................... 128/207.14, 207.15, 128/912, 348, 349 R, 349 BV, 350 R, 214 G, 276; 285/308, 420; 339/88 R, 90 R

[56] References Cited

U.S. PATENT DOCUMENTS 2,912,982 11/1959 Barsky ........................... 128/207.14
3,322,126 5/1967 Rusch et al. ................... 128/207.15

FOREIGN PATENT DOCUMENTS 649230 1/1951 United Kingdom ........... 128/207.14
8000997 5/1980 United Kingdom ........... 128/207.14

OTHER PUBLICATIONS

Cabal et al, Critical Care Medicine, vol. 7, No. 12, 1979.

Primary Examiner—Henry J. Recla

Attorney, Agent, or Firm—Armstrong, Nikaido, Marmelstein & Kubovcik

[57] ABSTRACT

A slip joint of an endotracheal tube comprising a slip joint body and a ring adaptor into which the slip joint body is insertable in close contact, the slip joint body being provided in its side wall with a L-slot having an upper open end, a width capable of passing a catheter to be used and a semicircular portion at the other end, the ring adaptor being provided in its side wall with an inverted L-slot having an upper or lower open end, the same width as that of the L-slot of the slip joint body and at the other end a semicircular portion of the same size as that of the semicircular portion in the L-slot of the slip joint body, and the ring adaptor being rotatable around the side wall of the slip joint body such that the semicircular portions in the L-slot and the inverted L-slot form a circular hole which has a diameter slightly smaller than the outer diameter of the catheter to be used and in which the catheter is hermetically inserted. By the use of this slip joint, there can be conducted, while supplying sufficient oxygen to the lung, the suction of secretions in the trachea and bronchi, determination of the position of the tip of a catheter inserted into the bronchi by a sound signal sent forth from the tip, determination of the pathological condition in the thorax by a sound signal sent forth from the tip of a catheter inserted in the bronchi, and collection of gas from the lung.

4 Claims, 16 Drawing Figures

SLIP JOINT OF ENDOTRACHEAL TUBE

BACKGROUND OF THE INVENTION

The present invention relates to a novel slip joint for an endotracheal tube, and more particular to a slip joint of endotracheal tube, by which the determination of the location of the tip of a catheter inserted into the bronchi and of a pathological condition in the thorax by means of a sound signal sent into the catheter, the suction of secretions in the trachea and bronchi and the monitoring of a gas in the lung can be conducted with ventilating.

In the field of clinical medicine, particularly in anaesthesia or artificial ventilation of patients with respiratory failure, it is very important for supplying a sufficient amount of oxygen to the lung to remove secretions such as sputum in the trachea and bronchi.

Figure 1:
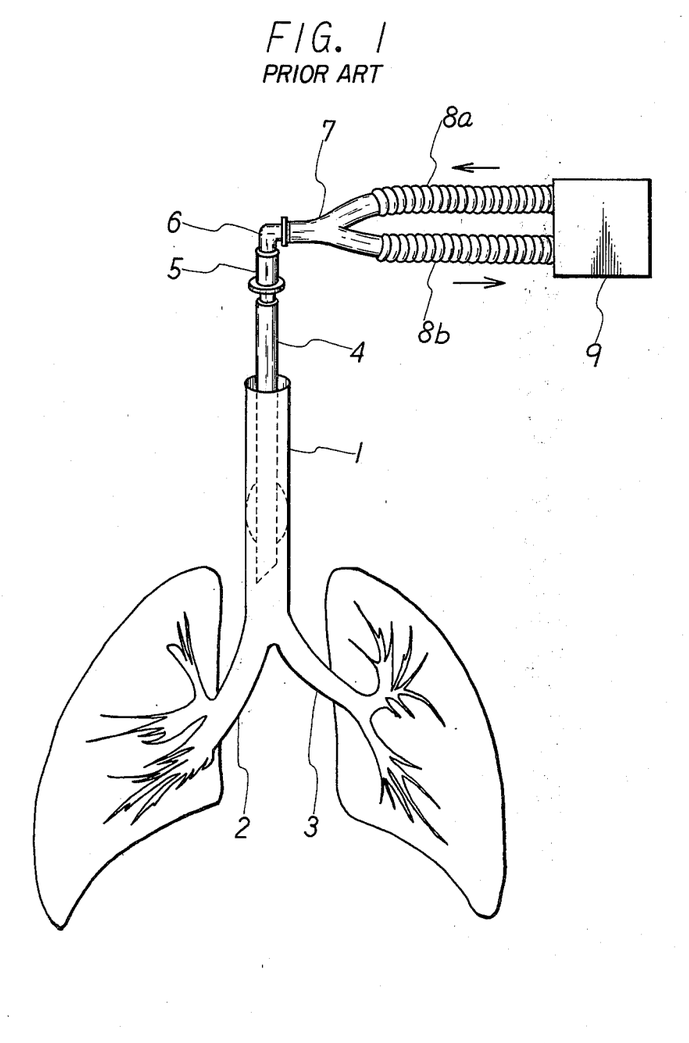
FIGS. 1 and 2 are illustrative views showing a connecting state of devices in conventional respiratory care.
Figure 2:
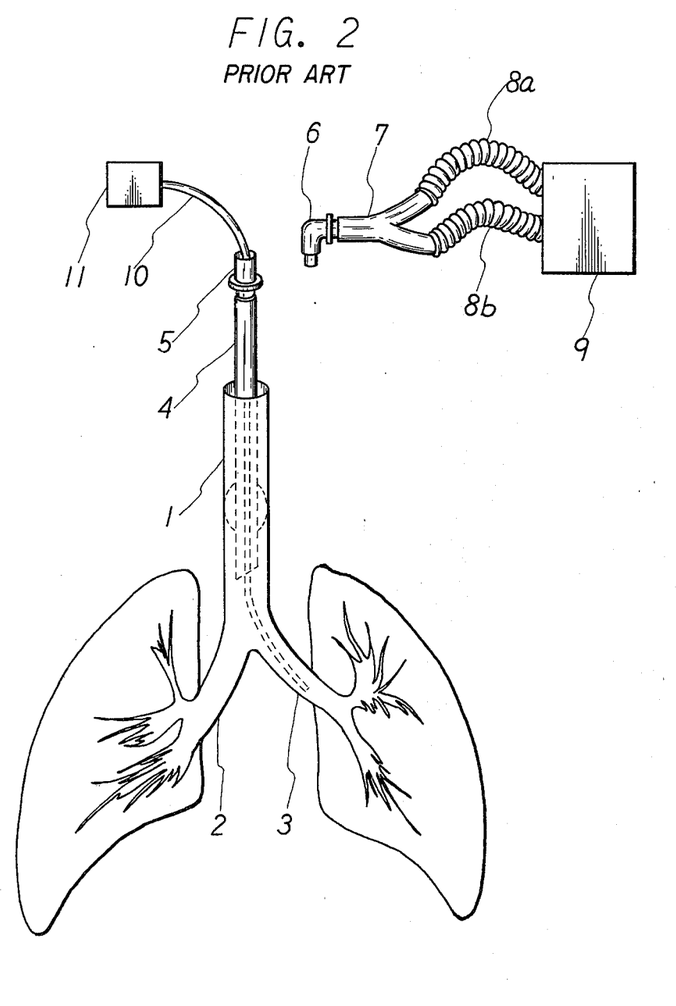

Hitherto, the removal of secretions in the trachea and bronchi by suction during anesthesia or artificial ventilation has been generally conducted in a manner as shown in FIGS. 1 to 2. FIG. 1 is an illustrative view showing the state that anaesthesia or artificial ventilation is conducted, and FIG. 2 is an illustrative view showing the state that the removal of secretions is conducted. In FIGS. 1 and 2, reference numeral 1 is trachea, reference numeral 2 is right bronchus, and reference numeral 3 is left bronchus. As shown in FIG. 1, an endotracheal tube 4 (the term "endotracheal tube" as used herein comprehending a tracheostomy cannula) is inserted into the trachea 1, and the proximal end of the endotracheal tube 4 is connected to a ventilator or anaesthetic machine 9 through a slip joint 5, an angle adaptor 6, a Y-shaped adaptor 7 and corrugate tubes 8a and 8b. The tube 8a is inspiratory tube and the tube 8b is expiratory tube. General anaesthesia or artificial ventilation is conducted in such a state. The suction of secretions is then conducted, as shown in FIG. 2, by detaching the angle adaptor 6 from the slip joint 5 to cut off the communication between the endotracheal tube 4 and the ventilator or anaesthetic machine 9, inserting a catheter 10 from the opening end of the slip joint 5 into the bronchus through the endotracheal tube 4, and connecting the proximal end of the catheter 10 to a suitable vacuum source 11.

Like this, the suction of secretions in the trachea and bronchi during anaesthesia or artificial ventilation has hitherto been conducted with disconnection of the ventilator or anaesthetic machine, that is to say, in the state that the ventilation is interrupted. Spontaneous respiration of a patient is often arrested by dosage of a muscle relaxant or other various drugs in order to conform the respiration of the patient with a ventilator during artificial ventilation and general anaesthesia or to make operative procedures easy. However, in such a case, disconnection of the ventilator or anaesthetic machine may plunge the patient into apnoea. When secretions in the trachea and bronchi is aspirated under such an apnoeic condition, a mixed gas such as $O_2+N_2$ or $O_2+N_2O$ in the lung is almost removed and the patient is plunged into hypoxic condition. Also, in case of respiratory care of a patient in a bad condition who raises a great deal of secretions, aspiration must be frequently done and it is reported that the frequent aspiration may cause bradycardia, tachycardia, various types of arrhythmia and cardiac arrest in hypoxic condition and is dangerous. Further, it is reported that in case of a patient with respiratory failure, particularly a newborn or infant of small lung capacity, all the gas in the lung is aspirated upon aspiration of secretions and the lung collapse (atelectasis) is caused. For these reasons, at present it is recommended to conduct the aspiration in such a manner as sufficiently ventilating the lung with 100% oxygen prior to aspiration, conducting aspiration procedure in as short time as possible, for instance, in 10 to 15 seconds, and sufficiently ventilating the lung with 100% oxygen immediately after aspiration, but this manner is troublesome.

Since the suction of secretions with the interruption of ventilation causes various troubles as stated above, it is also proposed to conduct the suction in a manner in which the angle adaptor is provided with a hole for inserting a suction catheter, and the catheter is inserted through the hole of the angle adaptor and the suction is conducted in the state that the endotracheal tube is communicated with the ventilator or anaesthetic machine. However, since the insertion hole is made larger than the outer diameter of the catheter in order to make the insertion of catheter easy, an inspiratory gas such as oxygen is leaked out from a gap between the catheter and the insertion hole. Therefore, it is impossible to ventilate the lung during the insertion of catheter and to aspirate secretions while supplying a sufficient amount of oxygen to a patient.

Accordingly, there is desired the development of a device enabling to aspirate secretions while ventilating and supplying sufficient oxygen to patients.

The present inventor previously developed a device capable of easily, exactly and safely determining the position of the distal end of a catheter inserted into the bronchus by sending a sound signal into the inserted catheter and receiving the sound signal sent forth from the distal end of the catheter, and thereby the selective suction of the left or right bronchus is possible, and a device capable of easily, exactly and safely determining the pathological condition in the thorax such as pulmonary edema, pleural effusion, hemothorax, pyothorax, pneumothorax or neoplasm of the lung by utilizing that the sound signal sent force from the tip of the catheter is attenuated until it reaches a sound signal receiver through the chest wall and the degree of the attenuation varies largely depending on the pathological condition. It is also desirable that the determination of the position of the tip of catheter and determination of the pathological condition in the thorax by such a device are conducted while ventilating the lung.

Further, in case of artificial ventilation over a long term, gas (oxygen and carbon dioxide) in the lung is continuously collected by a catheter of smaller calibre inserted into the lung than a suction catheter and the composition of the gas is monitored to determine whether the artificial ventilation is correctly conducted. In that case, it is also desirable to collect the gas while ventilating the lung.

SUMMARY OF THE INVENTION

It is an object of the present invention to provide a slip joint of an endotracheal tube whereby the suction of secretions in the trachea and bronchi, the determination of the position of the tip of a catheter inserted into the bronchus, the determination of a pathological condition in the thorax and the collection of the gas from the lung can be conducted while supplying sufficient oxygen to the lung.

The above and other objects of the present invention will become apparent from the description taken with the accompanying drawings.

In accordance with the present invention, there is provided a slip joint of an endotracheal tube or tracheostomy cannula comprising:

a slip joint body, said body being provided in its side wall with a L-slot having an upper open end and a width capable of passing a catheter to be used, and the other end of said L-slot being shaped in a semicircle slightly smaller than a semicircle of the cross section of the catheter to be used, and a ring adaptor attachable around the side wall of said slip joint body in close contact therewith, said adaptor being provided in its side wall with an inverted L-slot having an upper or lower open end and the same width as that of the L-slot of said slip joint body, the other end of said inverted L-slot being shaped in a semicircle having the same size as that of the semicircle at the end portion of the L-slot of said slip joint body, and said ring adaptor being movable around the side wall of said slip joint body such that the semicircular end portion of the L-slot of the slip joint body and the semicircular end portion of the inverted L-slot of the ring adaptor form a circular hole which has a diameter slightly smaller than the outer diameter of the catheter to be used and in which the catheter is hermetically inserted.

DETAILED DESCRIPTION

Referring to FIGS. 3(A), 3(B), 4 and 5, a slip Joint body 20 is composed of a cylindrical body 21 to be inserted into a ring adaptor 30 and to be connected to an angle adaptor, a cylindrical connection portion 22 to be connected to an endotracheal tube, and a flange 23 for preventing the falling out of the ring adaptor 30 and for making easy removal of the slip joint body 20. The flange 23 is usually provided with a non-slip means at the periphery. A L-slot 24 having a width capable of passing a catheter to be used is formed in the side wall of the cylindrical body 21, and its upper end is opened. The L-slot 24 is composed of a vertical slot 24a and a lateral slot 24b communicating with the sot 24a, and the end portion of the lateral slot 24b is shaped in a semicircle which is slightly smaller than the semicircle of the cross section of a catheter to be used to provide a semicircular portion 24c.

Figure 3A:
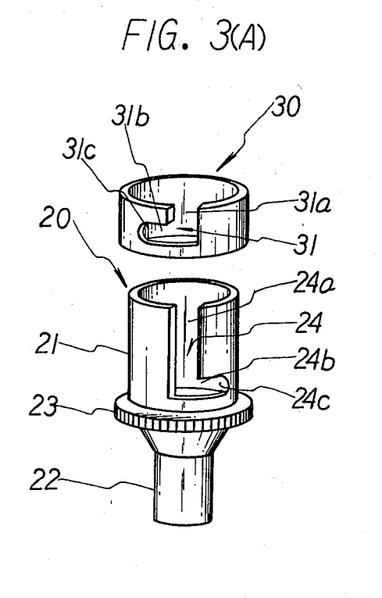
FIGS. 3(A) and 3(B) are perspective views showing embodiments of a slip joint being disassembled of the present invention.
Figure 3B:
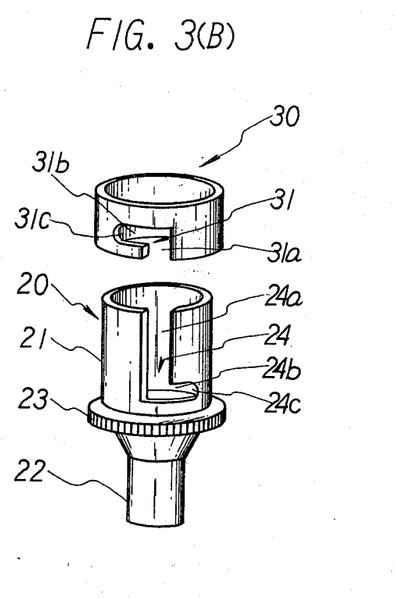
Figure 4:
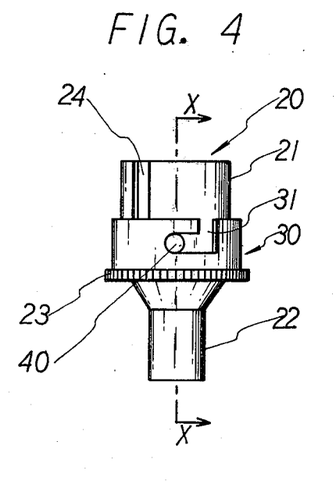
FIG. 4 is a front view of the slip joint shown in FIG. 3(A)
Figure 5:
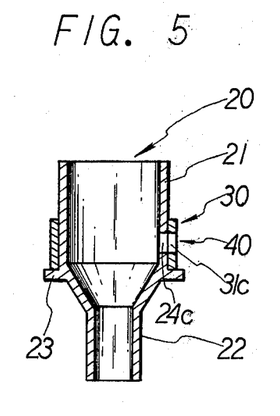
FIG. 5 is a section view taken on line X—X of FIG. 4.

The ring adaptor 30 is made so that the slip joint body 20 is inserted into the ring adaptor 30 in close contact with the inner surface of the adaptor 30, and the height of the adaptor 30 is smaller than that of the cylindrical body 21 of the slip joint body 20. An inverted L-slot 31 having the same width as that of the L-slot of the slip joint body 20 is formed in the side wall of the ring adaptor 30. The inverted L-slot 31 may be an inverted L-slot as shown in FIG. 3(A) having an open end at the upper end portion of the ring adaptor 30, or may be an inverted L-slot as shown in FIG. 3(B) having an open end at the lower end portion of the ring adaptor 30. The inverted L-slot 31 is composed of a vertical slot 31a and a lateral slot 31b communicating with the slot 31a, and the end portion of the lateral slot 31b is shaped in an adverse semicircle with respect to the semicircle 24c in the slip joint body 20 to provide a semicircular portion 31c having the same size as that of the semicircular portion 24c. FIG. 4 is a front view showing the state that the ring adaptor 30 is attached around the side wall of the slip joint body 20. When the ring adaptor 30 is put on the cylindrical body 21 of the slip joint body 20 and is moved so as to meet the semicircular portion 24c in the slip joint body 20 with the semicircular portion 31c in the ring adaptor 30, a circular hole 40 having a diameter slightly smaller than the outer diameter of a catheter to be used is formed. Metals and plastics are mentioned as materials of the slip joint body 20 and the ring adaptor 30.

Figures 6, 7:
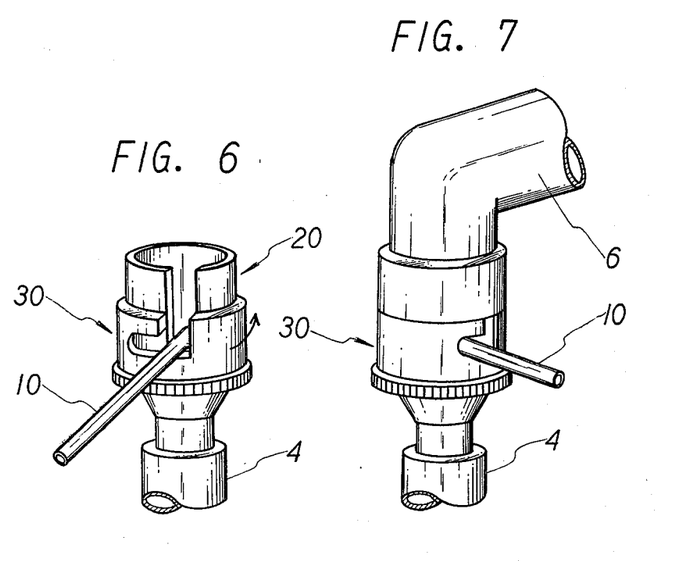
FIGS. 6 and 7 are perspective views showing a manner of placing a catheter in the slip joint shown in FIGS. 3(A), 4 and 5.

A manner of using the above-mentioned slip joint is explained with reference to FIGS. 6 and 7. An endotracheal tube 4 is connected with a ventilator or anaesthetic machine through the slip joint of the present invention (refer to FIG. 1), and artificial ventialtion or anaesthesia is then conducted. At that time, in order to prevent the leakage of a gas from the slip joint, the L-slot 24 of the slip joint body 20 and the inverted L-slot 31 of the ring adaptor 30 are positioned so that they do not overlap. When the use of a catheter is required, as shown in FIG. 6, the angle adaptor 6 is detached from the slip joint, and after squaring the vertical slot 24a of the slip joint body 20 with the vertical slot 31a of the ring adaptor 30, a catheter 10 is introduced to the opening of the slip joint body 20 and is inserted into the bronchus through the endotracheal tube 4. The proximal end portion of the catheter 10 is then put into the squared slots 24a and 31a and is located at the lower end portion thereof. In such a state, the ring adaptor is rotated in the arrow direction, so the catheter 10 is put in the state that it is inserted in a circular hole 40 formed by the semicircular portion 24c of the slip joint body 20 and the semicircular portion 31c of the ring adaptor 30. The angle adaptor 6 is then put on the cylindrical body 21 of the slip joint body 20 to fix it to the slip joint body 20. In such a manner, the endotracheal tube 4 and the ventilator or anaesthetic machine 9 are connected through the slip joint in the state that the catheter 10 is placed in the slip joint.

When the ventilator or anaesthetic machine is operated in such a state as shown in FIG. 7, there can be conducted, while ventilating the lung, the suction of secretions by the catheter 10 connected with a vacuum source, the determination of the position of the tip of the catheter 10 inserted into the bronchus and of the pathological condition in the thorax by the catheter 10 connected with a sound signal receiver, or monitoring of a gas in the lung by the catheter 10 connected with a monitor. When the use of the catheter 10 is interrupted, for instance, when the suction is not conducted, the catheter 10 may be choked by a clamp or detached from the slip joint.

According to the slip joint of the present invention, a catheter to be used is set up in the state that it is inserted in the circular hole 40 formed by the semicircular portion 24c of the slip joint body 20 and the semicircular portion 31c of the ring adaptor 30, and the circumference of the catheter at the insertion port is hermetically sealed because the circular hole 40 is slightly smaller than the outer diameter of the catheter. Therefore, there is no leakage of gas from the insertion port, and the suction of secretions, the determination of the position of the distal end of the catheter, the detection of the pathological condition in the thorax or the monitoring of gas in the lung can be conducted with supplying sufficient oxygen to the lung. Since it is possible to safely make treatment and diagnosis without plunging patients in hypoxia, the slip joint of the present invention makes a great contribution in the prevention and treatment of pulmonary complication and respiratory failure and in the respiratory care.

Figure 8:
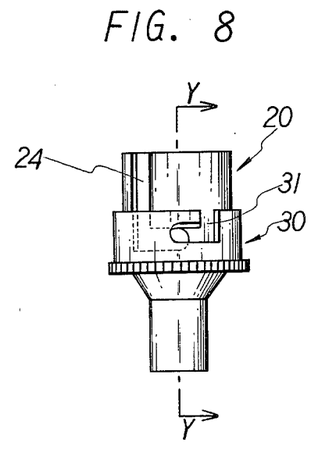
FIG. 8 is a front view showing another embodiment of a slip joint of the present invention.
Figure 9:
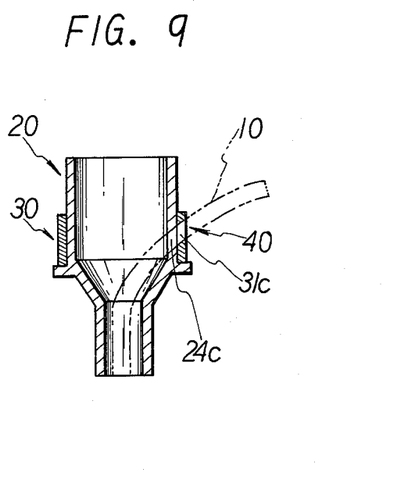
FIG. 9 is a section view taken on line Y—Y of FIG. 8.

FIG. 8 is a front view showing another embodiment of the slip joint of the present invention, and FIG. 9 is a section view taken on line Y—Y of FIG. 8. In this embodiment, the semicircular portion 24c of the L-slot 24 and the semicircular portion 31c of the inverted L-slot 31 are formed diagonally with a downward slant to the inside so that a circular hole 40 inclined inside and downward is formed by the semicircular portions 24c and 31c. Since the catheter 10 is set up along the oblique hole 40, it is smoothly bent in the slip joint without kinking.

Figure 10:
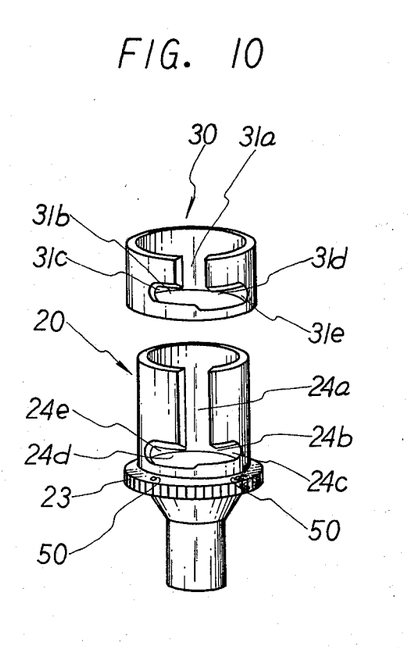
FIG. 10 is a perspective view showing a modification of a slip joint being disassembled of the present invention.
Figure 11A:
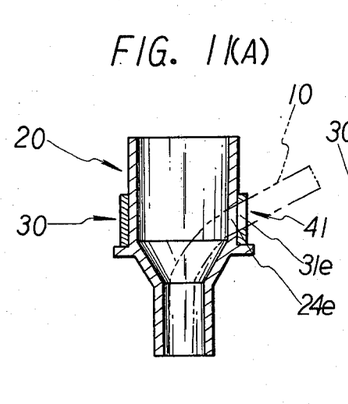
FIGS. 11(A) and 11(B) are section views of the slip joint shown in FIG. 10.
Figure 11B:
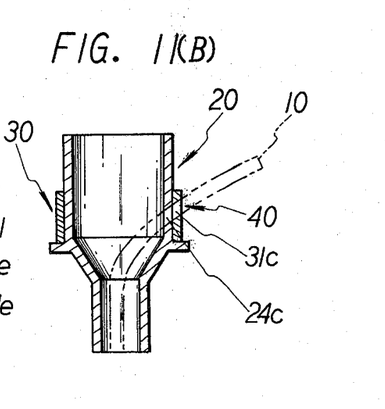

FIG. 10 is a perspective view showing another embodiment of the slip joint of the present invention. In this embodiment, T-slots are formed in the slip joint 20 and the ring adaptor 30. That is to say, on the opposite side to the lateral slot 24b in the slip joint body 20, a lateral slot 24d having a different width from that of the lateral slot 24b is also formed, and its end portion is shaped in a semicircle to provide a semicircular portion 24e having a different size from that of the semicircular portion 24c. On the other hand, a lateral slot 31d having the same width as that of the lateral slot 24d in the slip joint body 20 is formed on the opposite side to the lateral slot 31b in the ring adaptor 30, and its end portion is shaped in a semicircle to provide a semicircular portion 31e having the same size as that of the semicircular portion 24e in the slip joint body 20. As shown in FIGS. 11(A) and 11(B), when the semicircular portion 24e of the slip joint body 20 is met with the semicircular portion 31e of the ring adaptor 30, there is formed a circular hole 41 having a different diameter from that of the circular hole 40 formed by the semicircular portions 24c and 31c, and accordingly it is possible to hermetically insert into the hole 41 a catheter having a different diameter from that of a catheter to be inserted into the hole 40. The slip joint of this type is convenient, since it is possible to alternately use two kinds of catheters having different diameters, as occasion demands, by changing the combination of the semicircular portions 24c and 24e with the semicircular portions 31c and 31e. In the slip joint of this embodiment, the vertical slots 24a and 31a have a width through which a thicker catheter between two catheters used can pass.

It is also possible to use two kinds of catheters having different diameters in the embodiments shown in FIGS. 3(A), 3(B) and 8, when a L-slot having a different size from the L-slot 24 is further provided in the slip joint body 20 and another inverted L-slot corresponding to the above further L-slot is also provided in the ring adaptor 30. In that case, two catheters having different diameters can be simultaneously set.

Further, in the slip joint of the type as shown in FIG. 10, when an additional pair of T-slots are provided at another one place of each of the slip joint body 20 and the ring adaptor 30, it is possible to alternately set four kinds of catheters having different diameters, as occasion demands.

Figure 12:
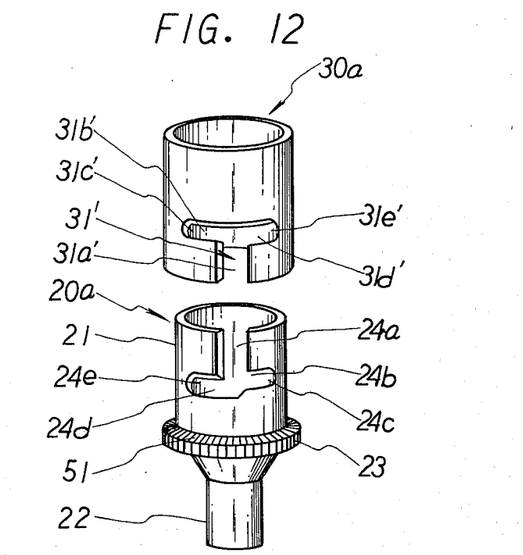
FIG. 12 is a perspective view showing another modification of a slip joint being disassembled of the present invention.
Figures 13, 14:
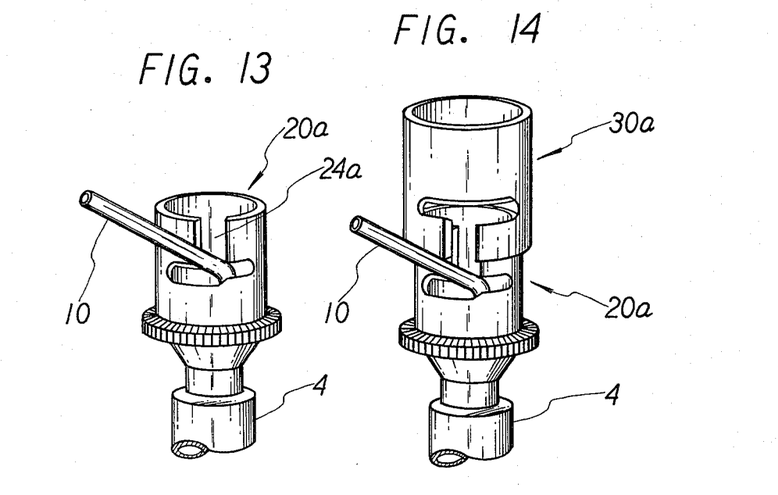
FIGS. 13 and 14 are perspective views showing a manner of placing a catheter in the slip joint shown in FIG. 12.

In the slip joint of the type shown in FIG. 12, a slip joint body 20a is similar to the slip joint body 20 shown in FIG. 11, but a ring adaptor 30a is higher than a cylindrical body 21 of the slip joint body 20a and is provided in its side wall with a T-slot 31 having a lower open end. The T-slot 31' is composed of a vertical slot 31a' and lateral slots 31b' and 31d', and at both ends of these lateral slots, semicircular portions 31c' and 31e' are formed. A catheter is fitted to the slip joint of this type in a manner as shown in FIGS. 13 and 14. That is to say, a catheter 10 is inserted from an opening of the slip joint body 20a of the slip joint connected to the proximal end of an endotracheal tube 4 into the bronchus through the endotracheal tube 4, and is placed in the vertical slot 24a. The ring adptor 30a is then set on the cylindrical body 21 of the slip joint body 20a with the vertical slot 31a' squared with the vertical slot 24a in the slip joint body 20a, and is then rotated so that the semicircular portion 31c' or 31e' meets the semicircular portion 24c or 24e in the slip joint body 20a. An angle adaptor to be connected with the slip joint in this embodiment may be an adaptor of a type such that it is put on or put in the ring adaptor 30a.

The height of the ring adaptor 30a in the embodiment shown in FIG. 12 may be smaller than the height of the cylindrical body 21 of the slip joint body 20a. In that case, there is of course used an angle adaptor of a type such that it is put on the slip joint body 20a.

In the present invention, the slip joint is preferably provided with a lock means for locking the ring adaptor 30 to the slip joint body 20 in the state that a catheter is set. Any usual means may be used as such a lock means. For instance, as shown in FIG. 10, projections 50 are provided on the upper surface of the flange 23, and on the other hand, depressions (not shown) corresponding to the projections are provided on the under surface of the ring adaptor 30 so that they mate with the projections to be locked. Also, as shown in FIG. 12, projections 51 provide radially on the upper surface of the flange 23 and depressions (not shown) provided radially on the under surface of the ring adaptor 30a so as to mate with the projections are employed as a lock means.

What is claimed is:

1. A slip joint of an endotracheal tube or a tracheostomy cannula comprising a slip joint body having opposing open ends and a passageway therebetween, means on one of said open ends adapted to be connected to an endotracheal tube or to a tracheostomy cannula, means on the other of said open ends adapted to be connected to a breathing gas source, said body being provided in its side wall with a L-slot having a first leg disposed in the direction of said passageway, said first leg having an upper open end terminating in said other of said open ends of said slip joint body and also having a width capable of passing a catheter therethrough to be used, and the other leg of said L-slot terminating in a semicircle slightly smaller than a semicircle of the cross section of a catheter to be used, and a ring adaptor slidably mounted around the side wall of said slip joint body in close contact therewith, said adaptor having opposing open ends and being provided in its side wall with an L-slot having a first leg disposed to align with the other leg of said L-shaped slot in said slip joint body, said first leg having an open end terminating in one of said opposing open ends of said ring adaptor and having the same width as the first leg of the L-slot of said slip joint body, the other leg of said L-slot in said ring adaptor being disposed to align with the other leg of said L-slot in said slip joint body and terminating in a semicircle having the same size as the semicircle at the end portion of the L-slot of said slip joint body, the other leg of said L-slot in said ring adaptor extending laterally from the first leg in a direction opposite to the direction in which the other leg of the L-slot in said slip joint body extends from its first leg, and said ring adaptor being movable around the side wall of said slip joint body such that the semicircular end portion of the L-slot in the slip joint body and the semicircular end portion of the inverted L-slot in the ring adaptor form a circular hole which has a diameter slightly smaller than the outer diameter of the catheter to be used and in which the catheter can be inserted and hermetically sealed.

2. The slip joint of claim 1, wherein the semicircular portions in said slip joint body and ring adaptor are inclined towards said one of said open ends of said slip joint body.

3. The slip joint of claim 1 or 2, wherein each L-slot of said slip joint body and ring adaptor also includes a third leg extending laterally from said first leg and in the opposite direction from said second leg, said third legs having a different width from that of said second legs and further terminate in a semicircle having a different size from the semicircle in said second legs whereby a catheter having a diameter different than the catheter which can be sealed in the second legs could be hermetically sealed in the third legs.

4. The slip joint of claim 1, wherein said slip joint body is provided with a lock means for locking the ring adaptor at a desired position.

* * * * *